US009696452B2

(12) United States Patent
Schafer et al.

(10) Patent No.: US 9,696,452 B2
(45) Date of Patent: Jul. 4, 2017

(54) VOLUMETRIC AND PROJECTION IMAGE GENERATION (71) Applicant: ANALOGIC CORPORATION, Peabody, MA (US)

(72) Inventors: David Schafer, Rowley, MA (US); Ram Naidu, Newton, MA (US); Serge Savard, Boston, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 14/440,436

(22) PCT Filed: Nov. 2, 2012

(86) PCT No.: PCT/US2012/063175
§ 371 (c)(1),
(2) Date: May 4, 2015

(87) PCT Pub. No.: WO2014/070191
PCT Pub. Date: May 8, 2014

(65) Prior Publication Data
US 2015/0260875 A1 Sep. 17, 2015

(51) Int. Cl.
*A61B 6/03* (2006.01)
*A61B 6/00* (2006.01)
(Continued)

(52) U.S. Cl.
CPC ............ *G01V 5/005* (2013.01); *A61B 6/032* (2013.01); *A61B 6/4266* (2013.01); *G01N 23/04* (2013.01); *G01N 23/046* (2013.01); *G01V 5/0008* (2013.01)

(58) Field of Classification Search
CPC ....... A61B 6/032; A61B 6/027; A61B 6/4014; A61B 6/4233; A61B 6/4266;
(Continued)

(56) References Cited

U.S. PATENT DOCUMENTS 4,365,339 A * 12/1982 Pavkovich ............ A61B 6/032
378/15
5,228,069 A * 7/1993 Arenson ............ A61B 6/4085
378/11
(Continued)

FOREIGN PATENT DOCUMENTS

WO 2006119426 A2 11/2006

OTHER PUBLICATIONS

International Search Report cited in related application No. PCT/US12/63175 dated Jul. 3, 2013, pp. 12.

*Primary Examiner* — David A Vanore
(74) *Attorney, Agent, or Firm* — Cooper Legal Group LLC (57) ABSTRACT Among other things, radiation systems and techniques for generating volumetric data and projections images of an object(s) under examination are provided. The radiation system comprises at least two detector arrays and at least one radiation source. During an examination, the radiation source and at least one detector array are rotated about the object while a second detector array is substantially fixed in place. In one embodiment, the radiation source is configured to, at times, illuminate the first detector array and, at times, illuminate the second detector array. For example, the radiation source may illuminate the first detector array during nearly all of the rotation while the second detector array is merely illuminated at a single gantry rotation angle. Information generated by the second detector array may be utilized to yield volumetric data while information generated by the first detector array may be utilized to yield a projection image, for example.

20 Claims, 7 Drawing Sheets (51) Int. Cl.
*G01V 5/00* (2006.01)
*G01N 23/04* (2006.01)

(58) Field of Classification Search
CPC ... A61B 6/4291; A61B 6/5235; A61B 6/4035; A61B 6/035; A61B 6/42; A61B 6/4258; A61B 6/4452; A61B 6/587; A61B 90/36; G01N 23/046; G01N 23/04; G01T 1/1644; G01T 1/2018
USPC .... 378/4, 19, 15, 62, 9, 11, 16, 205, 5, 901, 378/14, 145, 146, 147, 154, 158, 17, 177, 378/197, 207, 8, 98.2, 98.8; 250/367, 250/359.1, 360.1, 363.1, 368, 486.1, 250/487.1
See application file for complete search history.

(56) References Cited

U.S. PATENT DOCUMENTS

| | | | | |
|---|---|---|---|---|
| 5,365,565 | A * | 11/1994 | Barbaric | G03B 42/025 250/359.1 |
| 5,644,614 | A * | 7/1997 | Toth | A61B 6/032 378/145 |
| 5,712,483 | A * | 1/1998 | Boone | G01T 1/2018 250/367 |
| 6,185,271 | B1 * | 2/2001 | Kinsinger | A61B 6/032 378/19 |
| 6,215,844 | B1 * | 4/2001 | Adachi | A61B 6/032 378/19 |
| 6,415,012 | B1 * | 7/2002 | Taguchi | A61B 6/032 378/15 |
| 6,560,308 | B1 * | 5/2003 | Zmora | A61B 6/032 378/15 |
| 6,894,281 | B2 * | 5/2005 | Such | G01T 1/1644 250/363.1 |
| 7,753,586 | B2 * | 7/2010 | Oikawa | A61B 6/032 378/154 |
| 7,945,012 | B2 * | 5/2011 | Ye | A61B 6/032 378/11 |
| 8,483,352 | B2 * | 7/2013 | Hoffman | A61B 6/032 378/19 |
| 8,488,736 | B2 * | 7/2013 | Hoffman | A61B 6/032 378/19 |
| 2001/0012328 | A1 * | 8/2001 | Koppe | A61B 6/4014 378/62 |
| 2002/0085681 | A1 * | 7/2002 | Jensen | A61B 5/06 378/197 |
| 2002/0186871 | A1 * | 12/2002 | Grass | A61B 6/032 382/131 |
| 2003/0076920 | A1 * | 4/2003 | Shinno | A61B 6/032 378/4 |
| 2003/0128801 | A1 * | 7/2003 | Eisenberg | A61B 6/4291 378/19 |
| 2004/0086075 | A1 * | 5/2004 | Hein | A61B 6/032 378/4 |
| 2011/0080993 | A1 | 4/2011 | Hoffman et al. | |
| 2011/0080995 | A1 | 4/2011 | Hoffman et al. | |
| 2012/0063565 | A1 * | 3/2012 | Klingenbeck | A61B 6/00 378/9 |
| 2015/0223766 | A1 * | 8/2015 | Besson | G01T 1/2985 378/5 |
| 2015/0260875 | A1 * | 9/2015 | Schafer | A61B 6/032 378/4 |
| 2015/0297155 | A1 * | 10/2015 | Christensen | A61B 6/032 378/5 |
| 2016/0022237 | A1 * | 1/2016 | Hiraoka | A61B 6/032 378/9 |
| 2016/0128652 | A1 * | 5/2016 | Nagura | A61B 6/032 29/466 |

* cited by examiner

VOLUMETRIC AND PROJECTION IMAGE GENERATION

BACKGROUND

The present application relates to radiation systems. It finds particular application in the context of security imaging, where it may be desirable to display high resolution projection images representative of an object to security personnel while utilizing volumetric data representative of the object for automated threat detection. However, it may also find applicability in medical fields, industrial fields, and/or other fields where radiation systems are employed to examine/image an object.

Today, radiation systems (e.g., also referred to as imaging systems) such as computed tomography (CT) systems, single-photon emission computed tomography (SPECT) systems, projection systems, and/or line systems, for example, are useful to provide information, or images, of interior aspects of an object under examination. Generally, the object is exposed to radiation comprising photons (e.g., such as x-rays, gamma rays, etc.), and an image(s) is formed based upon the radiation absorbed and/or attenuated by interior aspects of the object, or rather an amount of photons that is able to pass through the object. Generally, highly dense aspects of the object absorb and/or attenuate more radiation than less dense aspects, and thus an aspect having a higher density, such as a bone or metal, for example, may be apparent when surrounded by less dense aspects, such as muscle or clothing.

Radiation systems are utilized in a variety of fields to image/examine aspects of an object not readily visible to the naked eye. For example, radiation systems are used in security applications to identify potential threat items, which may include weapons and/or explosives, concealed within a suitcase, bag, or person, for example. Two of the more commonly used radiation systems in security applications are CT systems and line-scan (or line) systems (e.g., or projection systems). Line systems are configured to view the object from a limited number of angles and generate projection images (e.g., two dimensional images) respectively representing a collapsed or flattened, two-dimensional view of the object (e.g., where the densities of aspects of an object through a line in which radiation travels are integrated and represented as a single point on the image). Such systems are particularly valuable for generating high resolution 2D images for display to security personnel responsible for identifying potential threat objects.

CT systems are configured to view an object from a plurality of angles (e.g., at least 180 degrees but often 360 degrees) and to generate volumetric data representative of the object. In this way, a 3D model of the object can be created and properties of respective aspects within the object, such as density information, z-effective information, shape characteristics, etc. can be determined. Using one or more of these properties, automated threat analysis can be performed to determine if the object is a potential threat item. Moreover, two-dimensional or three-dimensional images can be obtained from CT systems that are representative of the object (e.g., although typically such images are of a lower resolution than the projection images generated by line scanners due to differences in the resolution of CT detector arrays relative to detector arrays utilized in line and/or projection systems).

While automatic threat analysis algorithms have proven useful, such algorithms may, at times, mischaracterize an object, resulting in a false positive. In a security application this may result in non-threat objects being incorrectly classified as potential threats. Accordingly, items flagged as potential threat items may have to be resolved by some other method(s), such as a visual inspection of image(s), hand search of the items, and/or via use of some other screening technology.

SUMMARY

Aspects of the present application address the above matters, and others. According to one aspect, a radiation system is provided. The radiation system comprises a radiation source and a first detector array mounted to a rotating gantry of the radiation system. The rotating gantry is configured for rotation about an object during an examination of the object, and the first detector array is configured to generate information from which volumetric data indicative of the object is yielded. The radiation system also comprises a second detector array mounted to a first substantially stationary member of the radiation system. The second detector array is configured to generate information from which a projection image indicative of the object is yielded.

According to another aspect, a radiation system is provided. The system comprises a radiation source and a first detector array mounted to a rotating gantry. The rotating gantry is configured for rotation about an object during an examination of the object, and the first detector array is configured to generate information from which volumetric data indicative of the object is yielded. The system also comprises a second detector array mounted to a first substantially stationary member of the radiation system. The second detector array is configured to generate information from which a projection image indicative of the object is yielded. The radiation source is configured to illuminate the first detector array and the second detector array.

According to another aspect, method for threat detection is provided. The method comprises illuminating, via a single radiation source, a first detector array and a second detector array. The method also comprises utilizing volumetric data indicative of an object undergoing an examination and yielded from information generated by the first detector array to analyze whether the object is a potential threat object. The method also comprises providing for displaying a projection image representative of the object to a user, the projection image yielded from information generated by the second detector array.

Those of ordinary skill in the art may appreciate still other aspects of the present application upon reading and understanding the appended description.

FIGURES

The application is illustrated by way of example and not limitation in the figures of the accompanying drawings, in which like references generally indicate like elements and in which.

DESCRIPTION

The claimed subject matter is now described with reference to the drawings, wherein like reference numerals are generally used to refer to like elements throughout. In the following description, for purposes of explanation, numerous specific details are set forth in order to provide an understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to a radiation system, such as a security imaging system, for example, configured to generate projection images and volumetric data indicative of an object undergoing an examination and/or that underwent an examination. The radiation system comprises at least two detectors arrays and a radiation source. A first detector array and the radiation source are mounted on a rotating gantry configured to rotate about the object during the examination. By rotating about the object while detecting emitted radiation, the detector array can generate information from which volumetric data indicative of the object can be generated. A second detector array is mounted to a substantially stationary member and is configured to generate information from which one or more projection images indicative of the object can be generated. Typically, both the first detector array and the second detector are illuminated by the same (rotating) radiation source. Whereas the first detector array may be illuminated during nearly the entire rotation of the rotating gantry (e.g., causing the first detector array to be illuminated at a plurality of views), the second detector array is typically illuminated during merely a relatively small rotational segment of the rotating gantry (e.g., causing the second detector array to be illuminated at merely one view, during a relatively small rotational range, for a relatively short period of time, etc.).

It may be appreciated that by utilizing a first detector array configured for rotation about an object and a second detector array not configured for rotation about the object, the radiation system, in essence, comprises a projection system and a computed tomography (CT) system. That is, the rotation of the radiation source and the first detector array function in a manner similar to a CT system while the substantially stationary second detector array and limited illumination by the radiation source (e.g., from merely one view or gantry rotation angle) function in a manner similar to a projection system. In this way, a high resolution projection image (e.g., for display to security personnel) and volumetric data (e.g., for automated threat detection) indicative of an object may be generated using two detector arrays and a single radiation source, for example.

It may also be appreciated that the following systems and/or methods may find applicability to single energy systems and/or multi-energy systems. By way of example, the radiation source may be configured to emit two or more (distinct) energy spectra and/or at least one of the first detector array or the second detector array may be configured to detect multiple energy spectra. In this way, by measuring multiple (distinct) energy spectra, additional information about an object under examination, such as z-effective information, for example, may be derived, that may be unavailable if the system is a single energy system configured to measure merely a single energy spectrum, for example.

Figure 1:
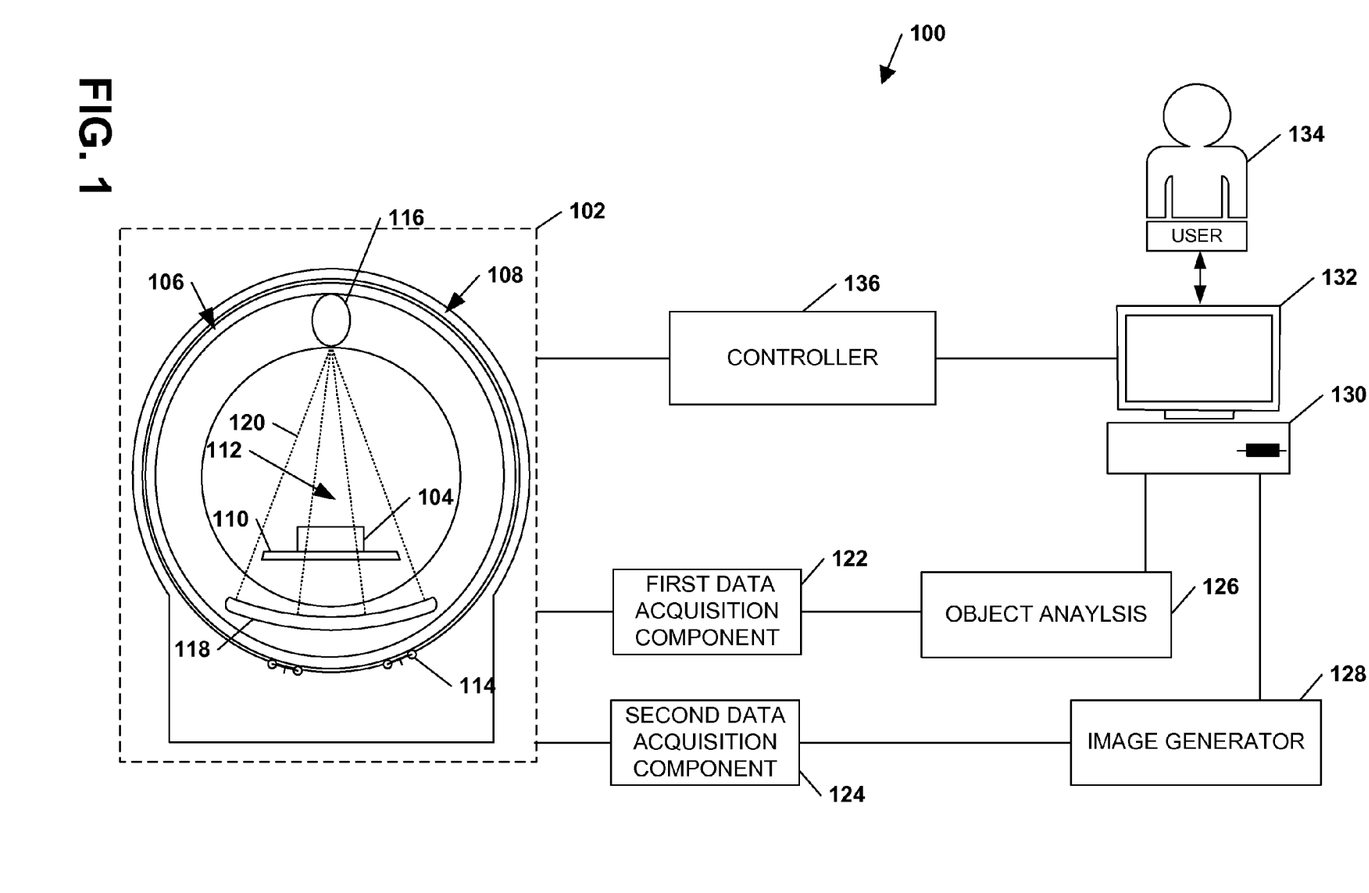
FIG. 1 is a schematic block diagram illustrating an example environment where a radiation system such as described herein may be implemented.

FIG. 1 illustrates an example environment 100 of a radiation system as provided for herein. It may be appreciated that the environment 100 merely provides an example arrangement and is not intended to be interpreted in a limiting manner, such as necessarily specifying the location, inclusion, and/or relative position of the components depicted therein. By way of example, a first data acquisition component 122 may be part of a first detector array 118 and/or a second data acquisition component 124 may be part of a second detector array (not shown), for example.

In the example environment 100, an examination unit 102 of the radiation system is configured to examine one or more objects 104. The examination unit 102 can comprise a rotating gantry 106 and a (stationary) support structure 108 (e.g., which may encase and/or surround at least a portion of the rotating gantry 106 (e.g., as illustrated with an outer, stationary ring, surrounding an outside edge of an inner, rotating ring)). During an examination of the object(s) 104, the object(s) 104 can be placed on a support article 110, such as a bed or conveyor belt, for example, that is selectively positioned in an examination region 112 (e.g., a hollow bore in the rotating gantry 106) configured to selectively receive the object(s) 104, and the rotating gantry 106 can be rotated and/or supported about the object(s) 104 by a rotator 114, such as a motor, drive shaft, chain, roller truck, etc.

The rotating gantry 106 may surround a portion of the examination region 112 and may comprise a radiation source 116 (e.g., an ionizing radiation source such as an x-ray source or gamma-ray source) and a first detector array 118 that is mounted on a substantially diametrically opposite side of the rotating gantry 106 relative to the radiation source 116. In this way, the relative position of the radiation source 116 and the first detector array 118 (e.g., the position of the radiation source(s) 116 relative to the detector array 118) may be maintained during an examination of the object(s) 104, for example.

Although not illustrated given that merely a cross-sectional view of the examination unit 102 is illustrated in FIG. 1, the examination unit 102 may also comprise a second detector array mounted to a first substantially stationary member of the stationary support structure 108, for example. As will be described below, the second detector array may be shaped differently than the first detector array 118 and information/data may be derived from the second detector array that is different than information/data derived from the first detector array 118, for example. Moreover, given the substantially stationary nature of the second detector array, a relative position of the radiation source 116 (e.g., mounted to the rotating gantry 106) and the second detector array may be varied during the examination of the object(s) 104, for example.

During the examination of the object(s) 104, the radiation source 116 emits cone, wedge, and/or other shaped radiation configurations from a focal spot(s) of the radiation source 116 (e.g., a region within the radiation source 116 from which radiation 120 emanates) into the examination region 112. It may be appreciated that such radiation 120 may be emitted substantially continuously and/or may be emitted intermittently (e.g., a brief pulse of radiation is emitted followed by a resting period during which the radiation source 116 is not activated).

As the emitted radiation 120 traverses the object(s) 104, the radiation 120 may be attenuated differently by different aspects of the object(s) 104. Because different aspects attenuate different percentages of the radiation 120, an image(s) may be generated based upon the attenuation, or variations in the number of photons that are detected by the first detector array 118 and/or the second detector array. For example, more dense aspects of the object(s) 104, such as a bone or metal plate, may attenuate more of the radiation 120 (e.g., causing fewer photons to strike the first detector array 118 and/or the second detector array) than less dense aspects, such as skin or clothing.

Typically, the radiation source 116 is configured to illuminate both the first detector array 118 and the second detector array. For example, in one embodiment, the radiation source 116 may be configured to illuminate the first detector array 118 during at least a first rotational segment of the rotating gantry 106 and to illuminate the second detector array during at least a second rotational segment of the rotating gantry 106. By way of example, the first detector array 118 may be illuminated during nearly an entire 360 degree rotation while the second detector array may be illuminated during merely 1 degree of the 360 degree rotation. Moreover, it may be appreciated that in some embodiments, the first detector array 118 and the second detector array may be illuminated concurrently (e.g., such as for the 1 degree rotational segment) while at other times merely one of the first detector array 118 or the second detector array may be illuminated at a time, for example.

Radiation detected by the first detector array 118 may be directly converted and/or indirectly converted into analog signals that can be transmitted from the first detector array 118 to a first data acquisition component 122 operably coupled to the first detector array 118. The analog signal(s) may carry information indicative of the radiation detected by the first detector array 118 (e.g., such as an amount of charge measured over a sampling period and/or an energy level of detected radiation). The first data acquisition component 122 may be configured to convert the analog signals into digital signals and/or to compile signals that were transmitted within a predetermined time interval, or measurement interval, using various techniques (e.g., integration, photon counting, etc.).

It may be appreciated that because the radiation source 116 and the first detector array 118 rotate about the object(s) 104, volumetric data indicative of the object(s) 104 may be yielded from the information generated by the first detector array 118. That is, stated differently, information or data representative of the information from a plurality of views or measurement intervals may be combined (e.g., in projection space or image space) to generate volumetric data indicative of (e.g., representative of) the object(s) 104. By way of example, with respect to the example environment 100, the radiation system comprises an object analysis component 126 configured to receive the digital data and generate volumetric data therefrom using analytical and/or iterative techniques known to those skilled in the art. In another embodiment, the radiation system may comprise an image reconstructor, and the image reconstructor may generate the volumetric data. In such an embodiment, the information or data may also be converted from projection space to image space using suitable analytical, iterative, or other reconstruction techniques (e.g., backprojection, iterative reconstruction, etc.).

Further, in one embodiment, the object analysis component 126 may utilize the volumetric data (e.g., in projection space and/or image space) to determine or estimate one or more properties of items within the object(s) 104. Based upon the at least some of the determined/estimated properties, the object analysis component 126 may determine if the object(s) 104 is a potential object of interest. That is, the object analysis component 126 may be configured to analyze the volumetric data to determine whether the object(s) 104 is a potential object of interest. By way of example, in a security environment, the object analysis component 126 (e.g., threat detection component) may be configured to approximate, among other things, density information, z-effective information, and/or shape characteristics of various items within the object (e.g., a suitcase, bag, etc.). Using such information/characteristics, the object analysis component 126 may determine if the object comprises a potential safety threat (e.g., such as a weapon and/or explosive). For example, the object analysis component 126 may compare the approximated densities of respective items to a list of densities for threat items. If one or more of the approximated densities corresponds to (e.g., matches within a specified deviation) a density on the list, the object analysis component 126 may alert security personnel of the correspondence (e.g., which may trigger additional, hands-on inspections of the object). In a medical application, for example, the object analysis component 126 may analyze the volumetric data to identify tumors, fractures, clots, etc. that may be identify based upon the volumetric data or based upon properties of the various aspects of the patient determined/estimated (e.g., derived) from the volumetric data.

Radiation detected by the second detector array 118 may be directly converted and/or indirectly converted into analog signals that can be transmitted from the second detector array to a second data acquisition component 124 that is operably coupled to the second detector array. The analog signal(s) carry information indicative of the radiation detected by the second detector array (e.g., such as an amount of charge measured over a sampling period and/or an energy level of detected radiation). The second data acquisition component 124 may be configured to convert the analog signals into digital signals and/or to compile signals that were transmitted within a predetermined time interval, or measurement interval, using various techniques (e.g., integration, photon counting, etc.). The information represented in the digital signals may be further transmitted to an image generator 128 configured to utilize the information to generate a projection image(s) indicative of the object(s) 104 using suitable image generation techniques, for example. In this way, one or more projection images indicative of the object(s) 104 may be yielded from information generated by the second detector array, for example.

The example environment 100 further comprises a terminal 130, or workstation (e.g., a computer), that may be configured to receive the projection image(s) indicative of the object (e.g., output by the image generator 128) and/or to receive information related to whether the object(s) 104 comprises items of potential interest, for example (e.g., output from the object analysis component 126). Further, in an embodiment where the information generated by the first detector array 118 is reconstructed into one or more images, such images may also be provided to the terminal 130. At least some of the received information/images may be provided by the terminal 130 for display on a monitor 132 to a user 134 (e.g., security personnel, medical personnel, etc.). In this way, the user 134 can inspect the image(s) to identify areas of interest within the object(s) 104 while also being provided information regarding potential items of interest that have be identified via an automated process, for example. The terminal 130 can also be configured to receive user input which can direct operations of the object examination unit 102 (e.g., a speed to rotate, a speed and direction of a support article 118, etc.), for example.

In the example environment 100, a controller 136 is operably coupled to the terminal 130. The controller 136 may be configured to control operations of the examination unit 102, for example. By way of example, in one embodiment, the controller 136 may be configured to receive information from the terminal 130 and to issue instructions to the examination unit 102 indicative of the received information (e.g., adjust a speed of a conveyor belt).

FIGS. 2-7 illustrate example arrangements of an examination unit (e.g., 102 in FIG. 1) comprising at least two detector arrays respectively illuminated by a same radiation source. It may be appreciated that the example arrangements are merely provided as samples and are not intended to limit the scope of the disclosure, including the scope of the claims, to the extent practical. Thus, other arrangements/configurations for the detector arrays and/or radiation source are also contemplated. It may also be appreciated that for purposes of brevity, similar features of respective arrangements may not be described with respect to each arrangement. Thus, unless explicitly stated otherwise, features described with respect to one arrangement may be applicable to the other arrangements, for example.

Figure 2:
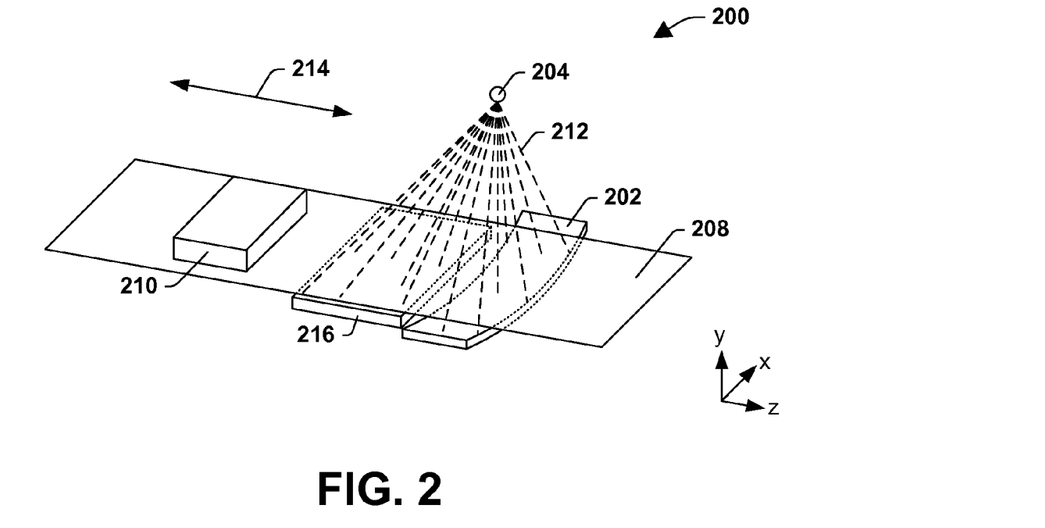
FIG. 2 illustrates an example arrangement of a radiation system.
Figure 3:
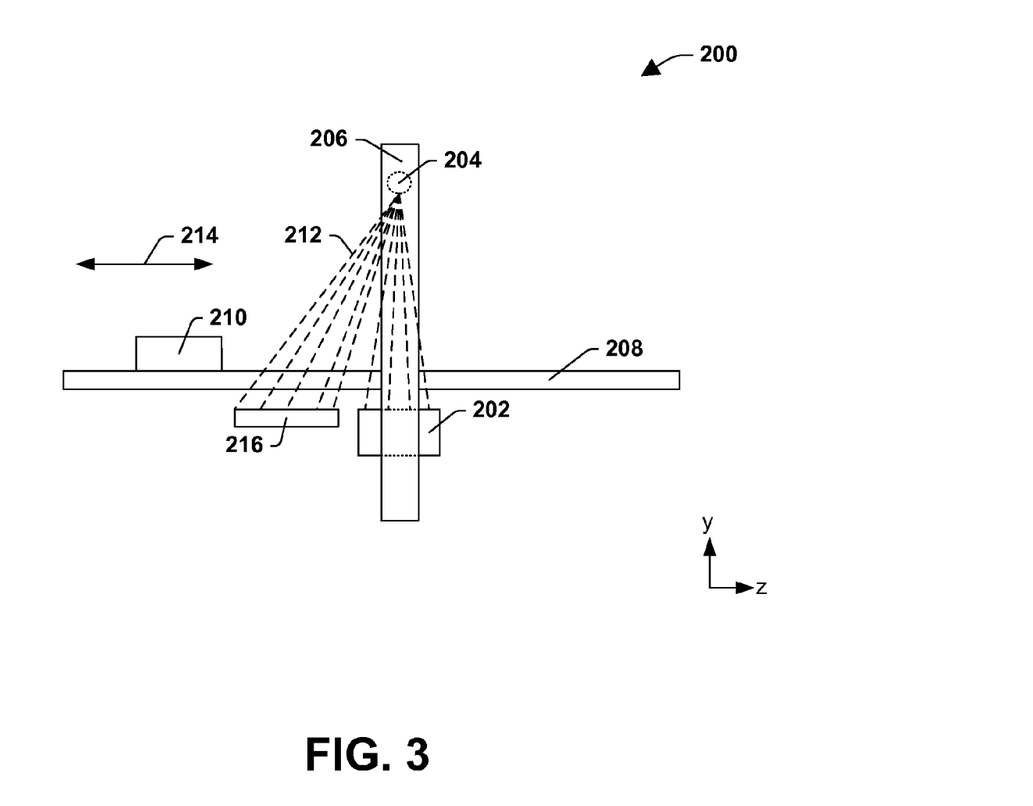
FIG. 3 illustrates an example arrangement of a radiation system.
Figure 4:
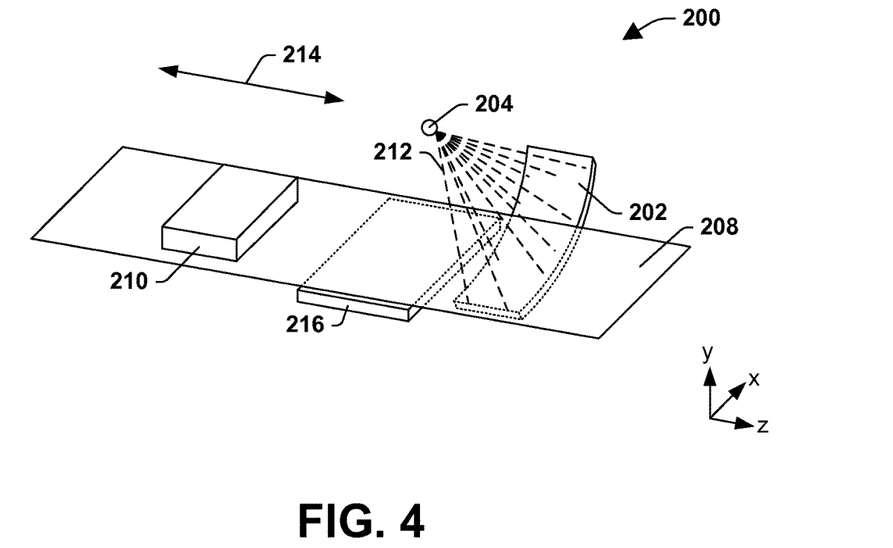
FIG. 4 illustrates an example arrangement of a radiation system.
Figure 5:
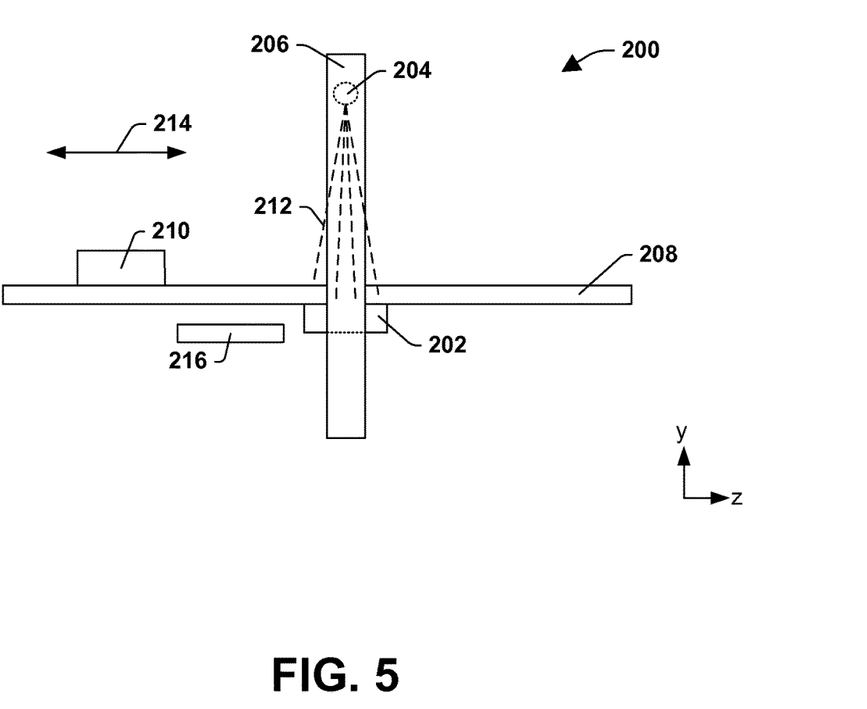
FIG. 5 illustrates an example arrangement of a radiation system.

With respect to FIGS. 2-5, a first example arrangement 200 of an examination unit is provided. More particularly, FIG. 2-3 illustrate the first example arrangement 200 when a rotating gantry 206 (e.g., 106 in FIG. 1) to which a radiation source 204 (e.g., 116 in FIG. 1) and a first detector array 202 (e.g., 118 in FIG. 1) are mounted is at a first gantry rotation angle (e.g., which may be arbitrarily defined as a 0 degree rotation angle). FIGS. 4-5 illustrate the first example arrangement 200 when the rotating gantry is at a second gantry rotation angle (e.g., which may be approximately 30 degrees given the arbitrarily defined 0 degree reference). FIGS. 2 and 4 illustrate the example arrangement 200 from a first viewpoint (e.g., above and to the side of the examination unit), and FIGS. 3 and 5 illustrate the example arrangement 200 from a second viewpoint (e.g., from the side of the examination unit).

For purposes of the instant application, a gantry rotation angle is generally defined as a number of degrees that the rotating gantry 206 has rotated away from a predefined zero-degree reference. For example, 0 degrees may be defined as a position of the rotating gantry 206 that causes the radiation source 204 to be positioned directly above a support article 208 (e.g., as illustrated in FIGS. 2-3). Thus, when the rotating gantry 206 rotates such that the radiation source 204 becomes positioned directly below the support article 208 (and such that the first detector array 202 becomes positioned directly above or over the support article 208), the gantry rotation angle may be approximately 180 degrees. Moreover, a rotational segment of the rotating gantry 206 may be defined as a segment of the rotation (e.g., or a range of one or more gantry rotation angles), for example. A rotational segment may be 1 degree, for example.

The rotating gantry 206 is configured to rotate about an axis of rotation while the support article 208 (e.g., 110 in FIG. 1) translates an object 210 (e.g., 104 in FIG. 1) through an examination region (e.g., a region through which radiation 212 is emitted). More particularly, in the example embodiment, the rotating gantry 206 is configured to rotate (e.g., in a plane parallel to a plane formed by the x-axis and y-axis) about an axis of rotation substantially parallel to a direction 214 in which the object 210 is translated during the examination (e.g., in the z-direction). In this way, a helical scan of the object is performed by the first detector array 202 (e.g., where the radiation source 204 and first detector array 202 do not move in the z-direction, and thus the helical trajectory is established by the combination of an x/y rotation of the radiation source 204 and first detector array 202 and the z-direction translation of the object 210). The rotation of the first detector array 202 relative to the object 210 facilitates the first detector array 202 viewing the object 210 from a plurality of angles, and the information generated by the first detector array 202 at the plurality of angles may be combined and/or synthesized to yield volumetric data indicative of the object, for example.

A second detector array 216 is mounted to a first substantially stationary member of the radiation system and/or examination unit of the radiation system and is configured to maintain a substantially static position relative to the support article 208 during the examination. Thus, the position of the second detector array 216 relative to the radiation source 204 and/or the first detector array 202 may change during an examination due to the rotation of the radiation source 204 and first detector array 202, for example.

The radiation source 204 is configured to (at times) illuminate the first detector array 202 and (at times) illuminate the second detector array 216. For example, at a first rotational segment (e.g., or at first gantry rotation angle) of the rotating gantry 206, the radiation source 204 may illuminate both the first detector array 202 and the second detector array 216. At another rotational segment of the rotating gantry 206 (e.g., or at a second gantry rotation angle as shown in FIGS. 4-5), merely one of the first detector array 202 or the second detector array 216 may be illuminated. In another embodiment, at no time during a rotation of the rotating gantry 206 may the radiation source 204 illuminate both the first detector array 202 and the second detector array 216. That is, stated differently, in another embodiment, when the radiation source 204 is illuminating the second detector array 216, the first detector array 202 may be exposed to little to no radiation, and when the radiation source 204 is illuminating the first detector array 202, the second detector array 216 may be exposed to little to no radiation.

Figure 8:
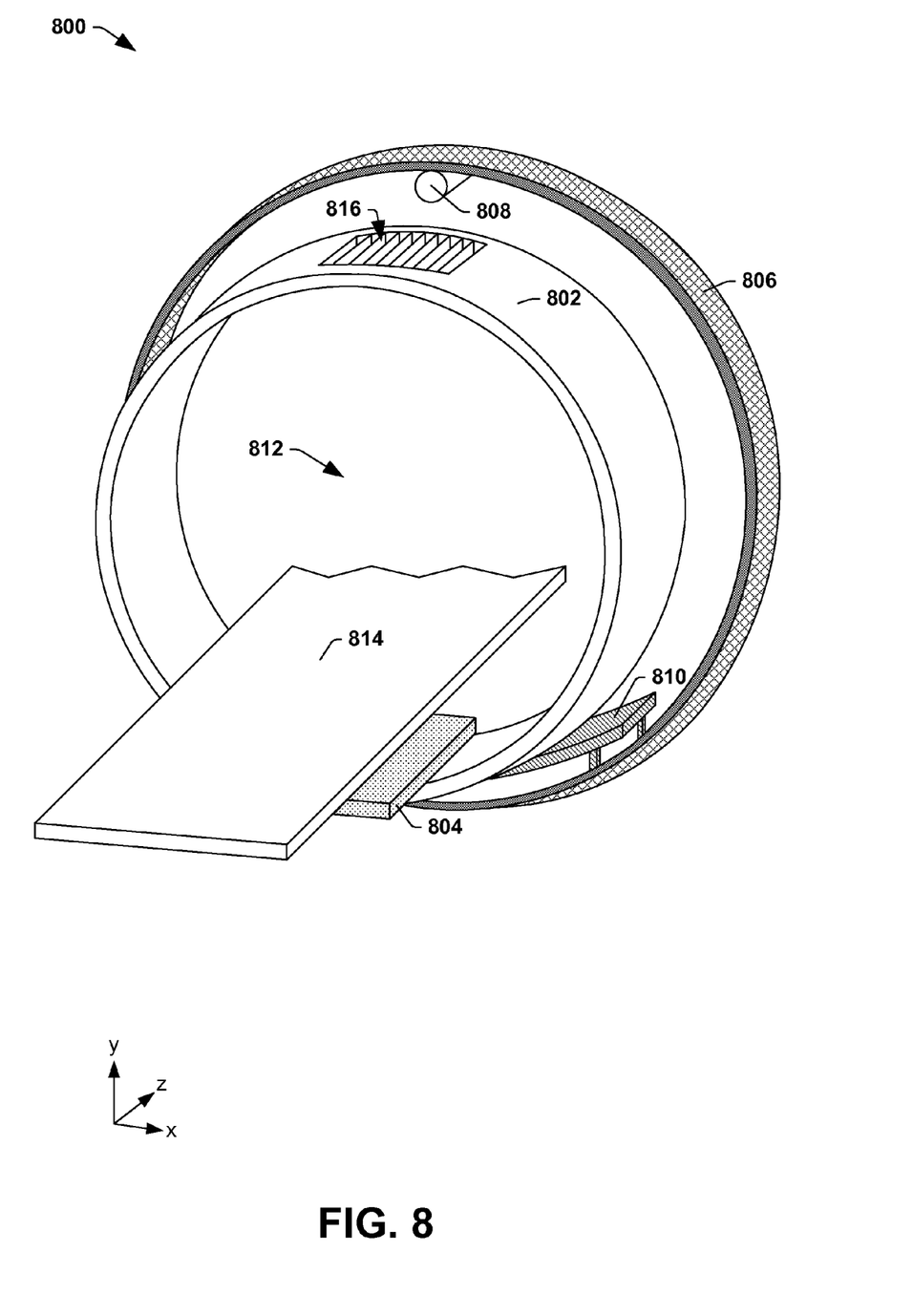
FIG. 8 illustrates an example arrangement of a radiation system.

A variety of techniques may be utilized to control illumination of the first detector array 202 and/or the second detector array 216. For example a pre-object collimator may be configured to control illumination of the second detector array 216. In one embodiment, such a pre-object collimator may be substantially stationary and may comprise an aperture (e.g., as shown in FIG. 8) that facilitates the illumination of the second detector array 216 when the rotating gantry 206 is at a specified gantry rotation angle or rotational segment and may attenuate radiation having a trajectory towards the second detector array 216 when the rotating gantry 206 is at other, non-specified gantry angles rotation angles, for example. In another embodiment, the pre-object collimator may be configured similar to a multi-leaf collimator and may dynamically adjust one or more leaves to control whether the first detector array 202 and/or the second detector array 216 is illuminated. In yet another embodiment, the radiation source 204 may be configured to rotate about an axis (e.g., extending in the x-direction) to illuminate the first detector array 202 during a first rotational segment of the rotating gantry 206 and to illuminate the second detector array 216 during a second rotational segment, for example.

It may be appreciated that controlling the illumination of the second detector array 216 may be useful because the second detector array 216 is configured to generate information from which a projection image indicative of an object undergoing an examination can be yielded. Such a projection image typically represents radiation 212 emitted at a fixed location (e.g., where the radiation source 204 is positioned diametrically opposite the second radiation detector 216 relative to the support article 208 and/or the object 210). In another embodiment, instead of or in conjunction with controlling the illumination of the second detector array 216, a sampling rate of the second detector array 216 may be such that samples acquired when the rotating gantry 206 (e.g., and thus the radiation source 204) is at a particular gantry rotation angle, or rotational segment, are utilized to generate the projection image while samples acquired when the rotating gantry 206 is at other gantry rotation angles, or other rotational segments, are discarded. In yet another embodiment, the second detector array 210 may be powered-up merely when the rotating gantry 206 is at a particular gantry rotation angle or rotational segment, for example. By way of example, a timing signal may be provided to the second detector array 216 to indicate when to power-up (e.g., or to indicate when the rotating gantry will be at a specified gentry rotation angle) and/or to indicate when to acquire a sample. In this way, what information is collected and/or how the information is processed may be controlled, as opposed to and/or in conjunction with controlling illumination of the second detector array 216, for example, The first detector array 202 and the second detector array 216 may be similarly configured or may be configured differently. For example, the second detector array 216 may be different from the first detector array in detector type and/or detector components. By way of example, in one embodiment, the first detector array 202 may be of a first detector type (e.g., an indirect conversion type) and the second detector array 216 may be of a second type (e.g., direct conversion type). In another embodiment, the first detector array 202 and the second detector array 216 may be of a same detector type (e.g., an indirect conversion type) but the components and/or composition of the detectors 202, 216 may vary. For example, the first detector array 202 may comprise a scintillator and readout electronics whereas the second detector array 216 may comprise a scintillator and digital camera, for example. In yet another embodiment, the first detector array 202 may be configured similarly to the second detector array 216. For example, both detector arrays 202, 216 may be indirect conversation arrays comprising a scintillator and readout electronics.

As another example, the size and/or arrangement of detector cells of the first detector array 202 may differ from the size and/or arrangement of detector cells of the second detector array 216. For example, as illustrated, the detector cells of the first detector array 202 may be arranged such that a detector surface (e.g., facing of the radiation source 204) of the first detector array 202 is substantially arcuate whereas the detector cells of the second detector array 216 may be arranged such that a detector surface of the second detector array 216 is substantially planar. Further, in another embodiment, the first detector array 202 may have a first detector cell density and the second detector array 216 may have a second detector cell density, which is different than the first detector cell density. For example, a 1 mm$^2$ portion of the first detector array 202 may comprise 1 detector cell whereas a 1 mm$^2$ portion of the second detector array 216 may comprise 2 or more detector cells (e.g., such that the density of cells within the second detector array 216 is greater than a density of cells within the first detector array 202). In this way, images results from the information produced by the second detector array 216 may have a higher spatial resolution than images produced by the first detector array 202, for example.

In one embodiment, a one-dimensional mask or two-dimensional mask may be inserted between the first detector array 202 and/or the second detector array 216 to filter a portion of the radiation spectrum of radiation 212 having a trajectory towards the first detector array 202 and/or the second detector array 216, for example. In this way, a spectral sensitivity of the first detector array 202 may be different than a spectral sensitivity of the second detector array 216, for example.

FIGS. 4-5 illustrate the first example arrangement 200 after the rotating gantry 206 has rotated a number of degrees (e.g., causing orientations of radiation source 204 and first detector array 202 relative to the support article 208 to be different in FIGS. 4-5 as compared with FIGS. 2-3). The second detector array 216 may remain substantially fixed during the rotation of the rotating gantry 206. For example, in the illustrated embodiment, the second detector array 216 remains substantially fixed below the support article 208.

As described with respect to FIGS. 2-3, whether the second detector array 216 is exposed to radiation may be a function of the gantry rotation angle. For example, when the gantry rotation angle is approximately 30 degrees, as illustrated in FIGS. 4-5, a pre-object collimator, for example, may mitigate illumination (e.g., exposure of radiation 212) to the second detector array 216. Thus, a cone-angle of radiation (e.g., an angle describing how the radiation 212 fans out in a direction (e.g., z-direction) parallel to the axis of rotation) may be less when the gantry rotation angle is approximately 30 degrees than when the gantry angle is approximately 0 degrees because the pre-object collimator may be configured to mitigate illumination of the second detector array 216 (e.g., and thus the radiation 212 fans in the z-direction out just enough to expose the detection surface of the first detector array 202 to radiation 212). As such, little to no information may be derived from the second detector array 216 when the gantry rotation angle is approximately 30 degrees.

The range of gantry rotation angles (e.g., or a size of the rotational segment) in which the second detector array 216 is illuminated may be predefined (e.g., and is typically small given the desire to create a projection image from the information generated by the second detector array 216). For example, in one embodiment, the second detector array 216 is illuminated for approximately a one-degree rotational segment of the rotating gantry 206. As such, exposure of the second detector array 216 to radiation during remaining degrees of the rotation (e.g., 359 degrees if the rotating gantry 206 completes at least one full rotation) may be mitigated. Moreover, where the rotating gantry 206 completes multiple rotations during an examination of the object 210, the second detector array 216 may be illuminated during respective occasions when the rotating gantry 206 returns to the specified/predetermined one-degree rotational segment, for example.

FIGS. 2-5 illustrate an example arrangement 200 where the rotating gantry 206 is oriented at an angle of 90 degrees relative to the direction of translation of the object 210. That is, stated differently, an axis of rotation for the rotating gantry 206 is substantially parallel to an axis/direction of translation causing the rotating gantry 206 to be tilted at an angle of 90 degrees relative to the direction of translation. By way of example with respect to FIG. 2, the axis of rotation and the direction of translation 214 respectively extend in the z-direction, while a plane within which the rotating gantry 206 rotates is substantially parallel to a plane extending through the x-axis and y-axis.

Figure 6:
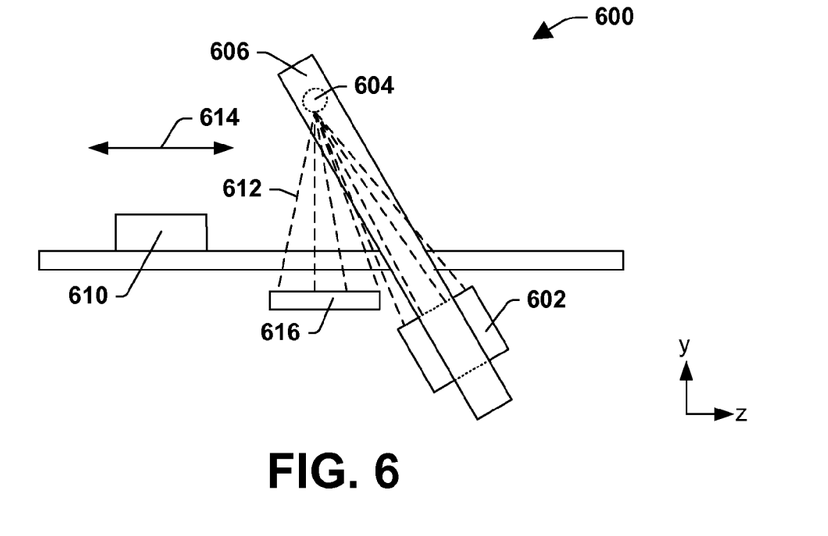
FIG. 6 illustrates an example arrangement of a radiation system.

FIG. 6 illustrates another example arrangement 600, where a rotating gantry 606 (e.g., 206 in FIG. 3) is oriented at an angle of other than 90 degrees relative to the direction of translation 614 (e.g., 214 in FIG. 3) of an object 610 (e.g., 210 in FIG. 2) undergoing an examination. In such an embodiment, the axis of rotation of the rotating gantry 606 may not be parallel to an axis/direction of translation. Further, in such an embodiment, a plane within which the rotating gantry 606 rotates may not be parallel to a plane extending through the x-axis and the y-axis. In CT applications, a configuration where the axis of rotation for the rotating gantry 606 is not parallel with the axis/direction of translation may be referred to as a (mechanically) tilted CT.

In one embodiment, a degree of the tilt (e.g., which may be defined as an angle between the axis of rotation and the direction of translation) may be a function of the placement of a second detector array 616 (e.g., 216 in FIG. 3). For example, in one embodiment, the rotating gantry 606 (e.g., and thus a radiation source 604 (e.g., 204 in FIG. 3) and a first detector array 602 (e.g., 202 in FIG. 3) mounted to the rotating gantry 606) may be tilted such that at least some radiation 612 (e.g., 212 in FIG. 3) impinges the second detector array 616 at a 90 degree angle (e.g., the angle measured between a detector surface of the second detector array 616 and the path of the radiation 612). As such, projection images derived from information generated by the second detector array 616 based upon the detected radiation may have less distortion, for example. By way of example, where, as in the illustrated embodiment, the second detector array 616 is exposed to radiation 612 when the radiation source 604 is directly overhead of the second detector array 616, an aperture used for the projection image could be vertical, thus producing a more vertical projection image (e.g., with less distortion than a projection image generated from an arrangement illustrated in FIGS. 2-5), for example.

It may be appreciated that in the foregoing arrangements, reference is made to merely two detector arrays. A first detector array configured to generate information from which volumetric data may be yielded and a second detector array configured to generate information from which a projection image may be yielded. In such an embodiment, a width of the second detector array (e.g., as measured in the z-direction) may be a function of, among other things, a pitch of the radiation system (e.g., where a pitch of the radiation system describes a speed of translation of the object). That is, stated differently, given that the second detector array may be illuminated during a (relatively small) rotational segment of the rotating gantry and given that the object is (continuously) translated during the examination, the second detector array is typically sized such that there is at least some overlap between a portion of the object viewed by the second detector array during a first rotation and a portion of the object viewed by the second detector array during a second rotation. Thus, a required width of the second detector array when the object traverses a large distance during one rotation may be greater than a required width of the second detector array when the object traverses less distance during one rotation. One technique for reducing a required width of the second detector array may be to position a plurality of detector arrays, respectively configured to generate information that can be utilized to yield a projection image, on one or more stationary member. That is, stated differently, information from a plurality of detector arrays may be combined to yield the projection image(s) indicative of the object. Such detector arrays may be similarity configured (e.g., have a similar cell density and/or arrangement, similar size, similar component arrangement, etc.) or may be configured differently, for example.

Figure 7:
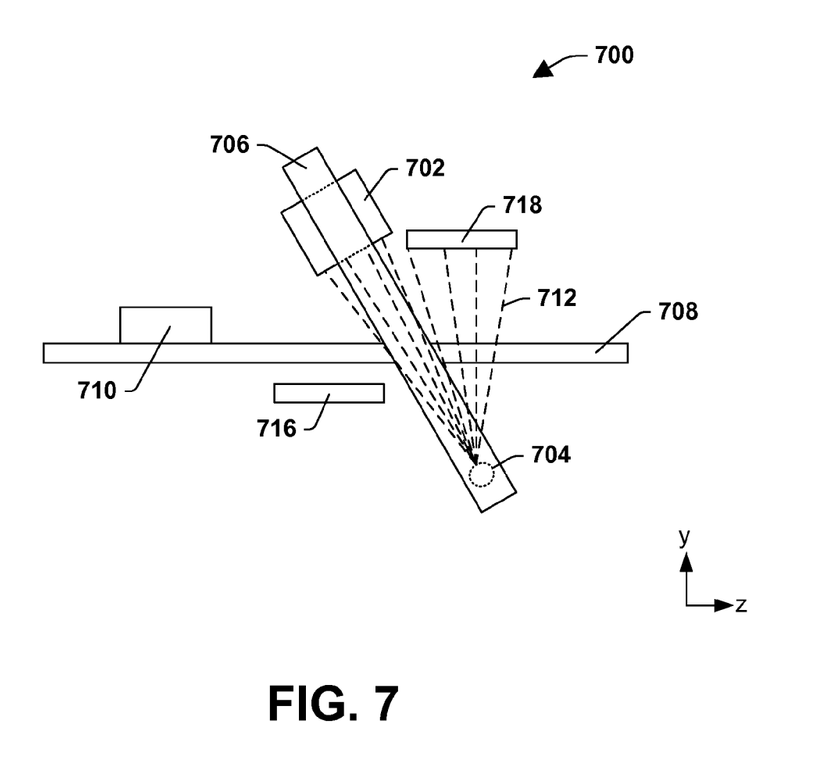
FIG. 7 illustrates an example arrangement of a radiation system.

FIG. 7 illustrates an example arrangement 700 of a radiation system comprising at least three detector arrays. A first detector array 702 (e.g., 602 in FIG. 2) and a radiation source 704 (e.g., 604 in FIG. 6) are mounted to a rotating gantry 706 (e.g., 606 in FIG. 6). A second detector array 716 (e.g., 616 in FIG. 6) is mounted to a first substantially stationary member, and a third detector array 718 is mounted to a second substantially stationary member (e.g., which may or may not be the same substantially stationary member to which the second detector array 716 is mounted). In this way, a relative position of the radiation source 704 and second detector array 716 and a relative position of the radiation source 704 and the third detector array 718 are varied during an examination of the object due to the rotation of the rotating gantry 706, for example. Typically, the second detector array 716 and the third detector array 718 are configured similarity (e.g., same composition, same size, same detector cell arrangement, etc.), but one or more features of the second detector array 716 may be different than a corresponding feature of the third detector array 718. For example, a width of the second detector array 716 may be different than a width of the third detector array 718.

In the illustrated embodiment, the second detector array 716 and the third detector array 718 are positioned 180 gantry rotation angles apart (e.g., such that a detection surface of the second detector array 716 faces upward on the page and a detection surface of the third detector array 718 faces downward on the page). As such, the second detector array 716 may be exposed to radiation 712 (e.g., 612 in FIG. 6) during a first rotational segment (e.g., as illustrated in FIG. 6 where the gantry rotation angle may be approximately 0 degrees), and the third detector array 718 may be exposed to radiation 712 during a second rotational segment (e.g., when the gantry rotation angle is approximately 180 degrees such that the radiation source 704 is positioned below a (e.g., substantially radiation transparent) support article 708 (e.g., 208 in FIG. 2)). It may be appreciated that by placing the third detector array 718 at a gantry rotation angle 180 degrees away from the second detector array 716, a projection image yielded from information generated by the second detector array 716 may be substantially stereotypic with a projection image yielded from information generated by the third detector array 718. In another embodiment, the third detector array 718 may be positioned at a gantry rotation angle that is not 180 degrees away from the second detector array 716.

Moreover, it may be appreciated that in the illustrated embodiment, the third detector array 718 is positioned on a substantially diametrically opposite side of the rotating gantry 706 relative to the second detector array 716. In another embodiment, the second detector array 716 and the third detector array 718 may be positioned on a same side of the rotating gantry 706 (e.g., such that a detection surface of the second detector array 716 faces a detection surface of the third detector array 718). Further, while reference is explicitly made to using two detector arrays to generate information from which a projection image is yielded, it may be appreciated that more than two detector arrays may be utilized for generating a projection image (e.g., with respective detector arrays being positioned at a different rotation angle and/or at a same rotation angle but on opposite sides of the rotating gantry 706).

FIG. 8 illustrates an example arrangement 800 of a radiation system which uses a pre-object collimator 802 to control illumination of a second detector array 804 (e.g., 216 in FIG. 2). In the example embodiment, the pre-object collimator 802 forms a ring or drum having a center of curvature that is approximately located at an axis of rotation for a rotating gantry 806 (e.g., 206 in FIG. 3). During an examination, the rotating gantry 806 is rotated relative to the pre-object collimator 802, which may be mounted to a substantially stationary member of the radiation system. In this way, a radiation source 808 (e.g., 204 in FIG. 2) and a first detector array 810 (e.g., 202 in FIG. 2) move or rotate relative to the pre-object collimator 802 during the examination.

Within a bore 812 of the pre-object collimator 802 is comprised a support article 814 (e.g., 208 in FIG. 2) and the second detector array 804, which may be mounted to the pre-object collimator, may be mounted to a same substantially stationary member as the pre-object collimator 802, and/or may be mounted to a different substantially stationary member of the radiation system.

The pre-object collimator 802 is comprised of a radiation attenuating material(s), such as lead and/or tungsten, for example, configured to absorb or scatter radiation impinging the pre-object collimator 802. As illustrated, the pre-object collimator 802 defines one or more apertures 816 (e.g., holes or windows) through which radiation may traverse the pre-object collimator 802 and illuminate the second detector array 804 (e.g., situated beneath the substantially radiation transparent support article 814). Thus, when the radiation source 808 is positioned such that radiation emitted from radiation source 808 has a trajectory through the aperture(s) 816, the second detector array 804 may be illuminated. When the rotating gantry 806 is rotated, causing the radiation source 808 to be repositioned relative to the pre-object collimator 802, radiation emitted from the radiation source 808 may not follow a path that extends through the aperture(s) 816. Thus, when the radiation source 808 is repositioned, the second detector array 804 may be exposed to little to no radiation. Typically, the aperture(s) 816 is positioned on a substantially diametrically opposite end of the pre-object collimator 802 relative to the second detector array 804.

In this illustrated embodiment, the one or more apertures are respectively separated by a slat of radiation attenuating material (e.g., creating a pergola-like design). In this way, an amount of illumination experienced by the second detector array 804 may be mitigated as the rotating gantry 806 approaches a desired gantry rotation angle and/or rotational segment and/or moves away from a desired gantry rotation angle and/or rotational segment (e.g., facilitating full exposure at a desired gantry rotation angle and little to no exposure at angles approximate the desired gantry rotation angle).

It may be appreciated that the foregoing pre-object collimator 802 is merely one example of one pre-object collimator design configured to control illumination of the second detector array 804 and that other designs/configurations are contemplated. For example, in another embodiment, the pre-object collimator may have a similar structure to the foregoing pre-object collimator 802, but the second detector array 804 may be placed adjacent an exterior surface of the pre-object collimator 802 as opposed to within the bore 812 (e.g., such that the pre-object filter 802 is situated between the detector array 804 and the support article 814 as opposed to the detector array 804 being situated between the pre-object filter 802 and the support article 814 as illustrated in FIG. 8). In such an embodiment, the pre-object collimator may be further configured to function as a pre-object mask that filters at least some of the radiation spectrum of radiation emitted by a radiation source, for example. In still another embodiment, the pre-object collimator may be a multi-leaf collimator or other dynamically adjustable pre-object collimator configured to adjust a cone-angle of the radiation as the rotating gantry rotates. In such an embodiment, the pre-object collimator may be positioned on the rotating gantry as opposed to on a substantially stationary member, for example.

Figure 9:
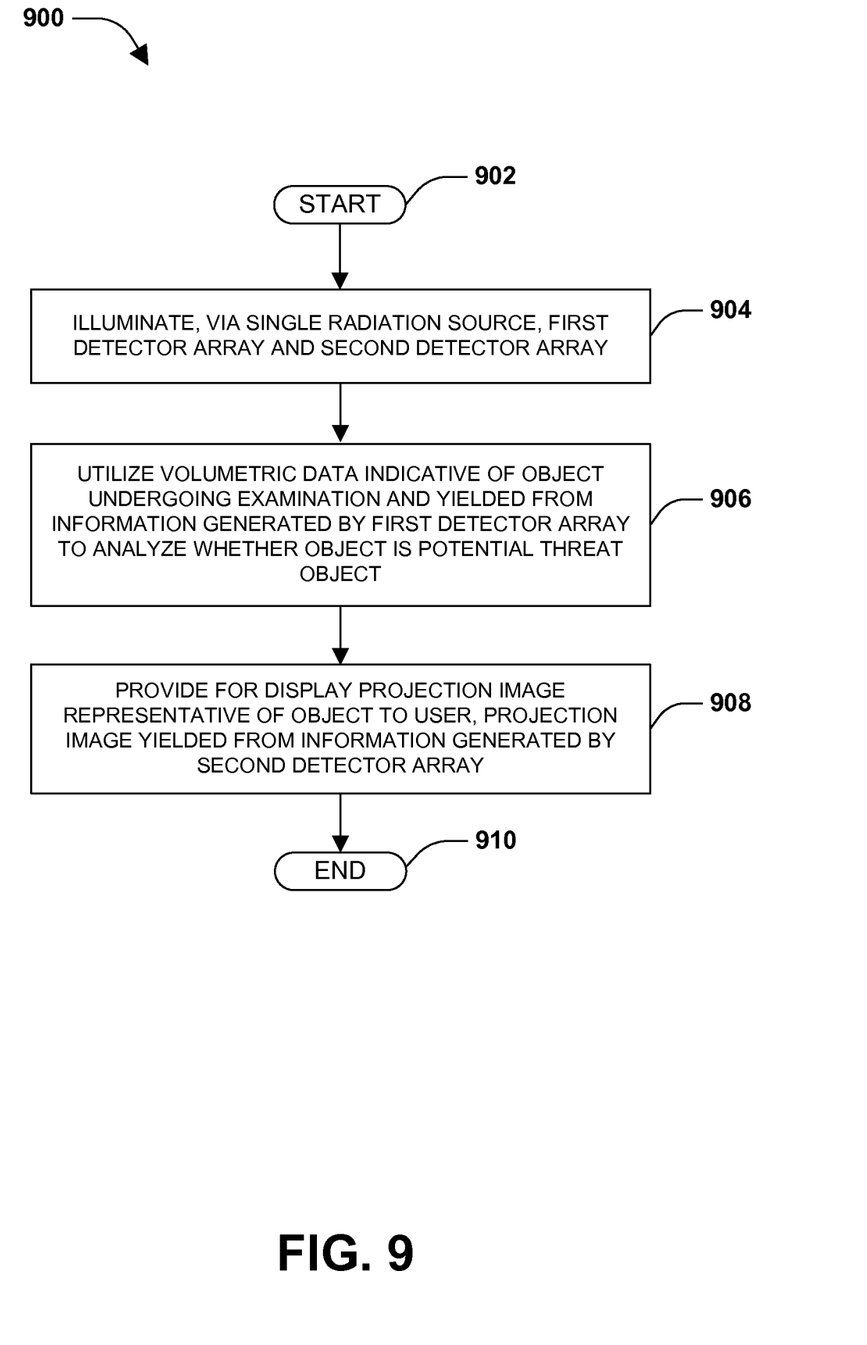
FIG. 9 is an example flow diagram illustrating an example method for threat detection.

FIG. 9 illustrates an example method 900 for threat detection. It may be appreciated that while reference is specifically made to threat detection, such a method 900 may be applied to identify items within objects in a non-security environment as well. For example, in medical application, the example method 900 may be utilized to identify particular items within a patient such as particular types of cells, blood cotes, etc., that can be identified based upon density information, z-effective information, shape information, or other information that is identifiable and/or derivable from volumetric data acquired from a computed tomography (CT) scan of the patient.

The example method 900 begins at 902 and a first detector array and a second detector array are illuminated via a single radiation source at 904. Typically, the radiation source and the first detector array are mounted to a rotating gantry and are configured to rotate about an object during an examination of the object (e.g., to view the object from a plurality of perspectives). As such, the first detector array may be illuminated during a first rotational segment of the rotating gantry and the second detector array may be illuminated during a second rotational segment of the rotating gantry. Typically, the first rotational segment is substantially larger than the second rotational segment (e.g., which may measure 1 degree of the rotation). Moreover, it may be appreciated that the first rotational segment and the second rotational segment may be least partially overlapping. By way of example, in one embodiment, a full rotation may be considered to be 360 degrees, and the first detector array may be exposed to radiation during the full rotation (e.g., meaning the first rotational segment measures 360 degrees). The second detector array may be exposed to radiation during merely a portion of the full rotation, such as during merely one degree of the full rotation (e.g., meaning the second rotational segment measurement 1 degree). As such, during the one degree in which the second detector array is illuminated, the radiation source is concurrently illuminating the first detector array and the second detector array. During the other approximately 359 degrees of the rotation, merely the first detector array may be illuminated, for example.

Whereas the first detector array and the radiation source are configured to rotate about the object, the second detector array is typically mounted to a substantially stationary member of the radiation system and is thus not configured for movement during the examination of the object. That is, stated differently, a relative position of the radiation source and the second detector array may be varied during an examination of the object while a relative position of the radiation source and first detector array may be maintained. It may be appreciated that the rotation of the first detector array (e.g., relative to the object) may cause the first detector array to view the object from a plurality of angles and facilitate the generation of information from which volumetric data indicative of the object can be generated. Conversely, the substantially stationary nature of the second detector array may cause the second detector array to view the object from a limited number of angles. As such, the information generated by the second detector array may be insufficient from which to generate volumetric data indicative of the object. Instead, the information may be merely sufficient to generate a two-dimensional projection image (e.g., representative of a single (e.g., top-down or bottom-up) view of the object.

At 906 in the example method 900, the volumetric data indicative of the object undergoing examination and yielded from information generated by the first detector array is utilized to analyze whether the object is a potential threat object. That is, stated differently, properties of individual (e.g., or compound) items within the object are estimated or derived from the volumetric data, and at least some of these properties are utilized to determine whether the object is a potential threat object or comprises a potential threat item. By way of example, the volumetric data may be utilized to estimate/approximate densities properties, z-effective properties, shape properties, and/or other attributes/characteristics of respective items comprised within the object. At least some of these properties/characteristics may then be utilized to determine a probability that the object comprises a potential threat item. For example, density information or z-effective information for respective items may be compared to a table of density values and/or z-effective values for weapons, chemicals, or other specified threat items. If the density information or z-effective information for one or more items is within a specified deviation of the density values and/or z-effective values for one or more specified threat items, the object may be labeled/categorized as a potential threat item and may be subjected to additional screening, for example.

At 908 in the example method 900, a projection image representative of the object is provided for display to a user. The projection image is yielded from information generated by the second detector array and typically has a spatial resolution that is higher than the spatial resolution of images obtainable from the information yielded by the first detector array. In this way, a high resolution two-dimensional image indicative of the object is provided for display to a user while volumetric data indicative of the object is utilized for automated threat detection, for example. It may be appreciated that the volumetric data may also be reconstructed into one or more images for display to a user (e.g., but typically such images are of a lower spatial resolution than the projection image yielded from information provided by a substantially stationary second detector array).

The example method 900 ends at 910.

Figure 10:
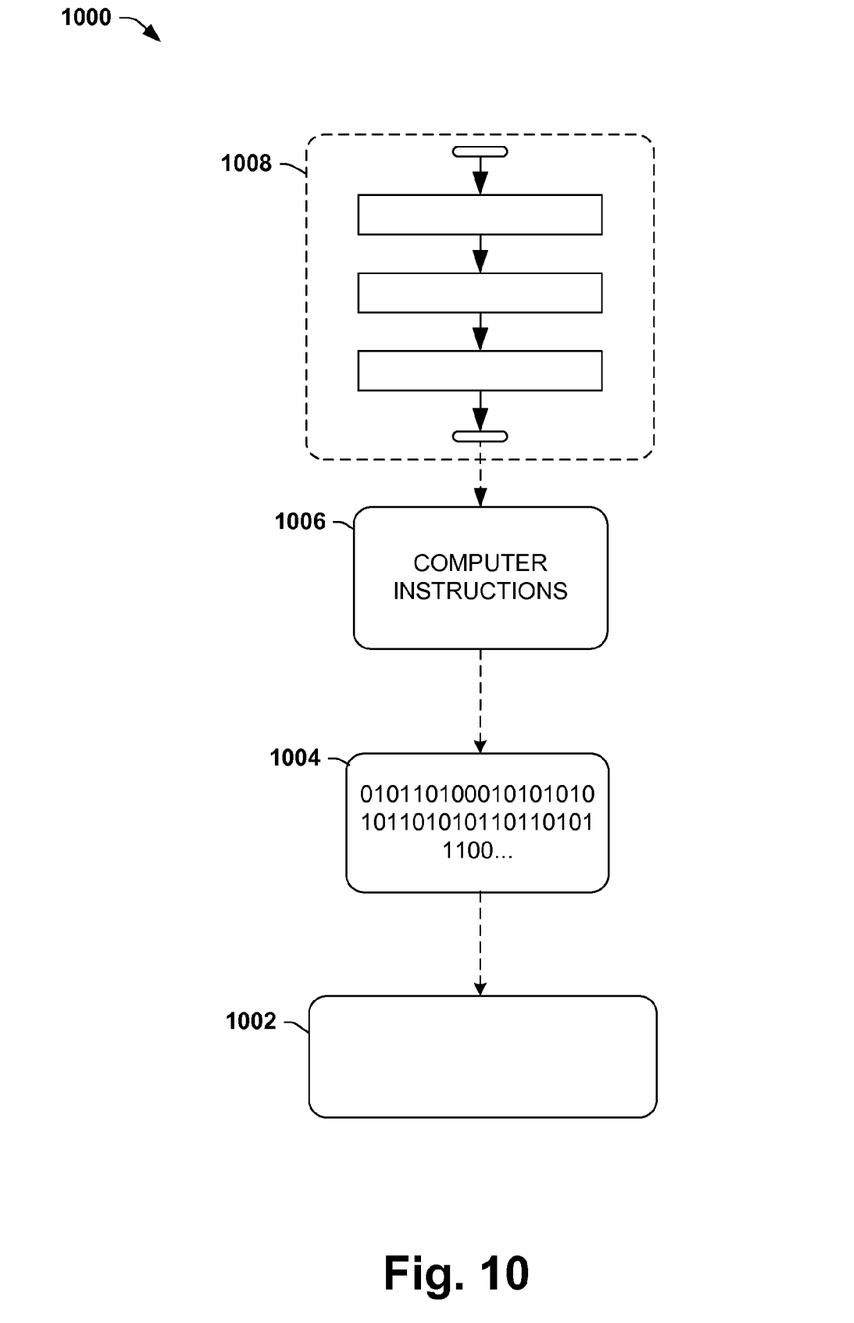
FIG. 10 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 10, wherein the implementation 1000 comprises a computer-readable medium 1002 (e.g., a flash drive, CD-R, DVD-R, application-specific integrated circuit (ASIC), field-programmable gate array (FPGA), a platter of a hard disk drive, etc.), on which is encoded computer-readable data 1004. This computer-readable data 1004 in turn comprises a set of computer instructions 1006 configured to operate according to one or more of the principles set forth herein. In one such embodiment 1000, the processor-executable instructions 1006 may be configured to perform a method 1008, such as at least some of the example method 900 of FIG. 9, for example. In another such embodiment, the processor-executable instructions 1006 may be configured to implement a system, such as at least some of the exemplary environment 100 of FIG. 1, for example. Many such computer-readable media may be devised by those of ordinary skill in the art that are configured to operate in accordance with one or more of the techniques presented herein.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used in either the detailed description or the claims, such terms are intended to be inclusive in a manner similar to the term "comprising".

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B" or two different (or identical) channels).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application.

What is claimed is:

1. A radiation system, comprising
   a stationary member;
   a rotating gantry configured to rotate relative to the stationary member;
   a radiation source mounted to the rotating gantry;
   a first detector array mounted to the rotating gantry; and
   a second detector array mounted to the stationary member.

2. The radiation system of claim 1, wherein the radiation source is configured to illuminate the first detector array and the second detector array.

3. The radiation system of claim 1, comprising a conveyor belt, wherein the second detector array is mounted to the stationary member under the conveyor belt.

4. The radiation system of claim 1, wherein:
   a detection surface of the first detector array is substantially arcuate, and
   a detection surface of the second detector array is substantially planar.

5. The radiation system of claim 1, comprising a pre-object collimator configured to attenuate radiation impinging thereon and configured to control illumination of the second detector array via the radiation source.

6. The radiation system of claim 5, wherein the pre-object collimator comprises a plurality of adjustable leaves that together define an aperture through which radiation emitted by the radiation source travels to control illumination of the second detector array.

7. The radiation system of claim 3, wherein:
   the conveyor belt extends in a first direction to convey an object in the first direction, and
   the second detector array is offset from the first detector array in the first direction.

8. The radiation system of claim 1, wherein the first detector array has a first detector cell density and the second detector array has a second detector cell density, the first detector cell density different than the second detector cell density.

9. The radiation system of claim 1, comprising a third detector array mounted to the stationary member.

10. The radiation system of claim 1, wherein the rotating gantry rotates about an axis of rotation, the axis of rotation not parallel to a direction in which an object is translated during an examination.

11. The radiation system of claim 9, comprising a conveyor belt wherein:
   the second detector array is mounted to the stationary member under the conveyor belt, and
   the third detector array is mounted to the stationary member over the conveyor belt.

12. A radiation system, comprising:
   a stationary member;
   a rotating gantry configured to rotate relative to the stationary member;
   a support article extending through a bore defined by the rotating gantry, wherein:
      a top surface of the support article, upon which an object under examination rests, lies in a first plane, and
      the rotating gantry rotates in a second plane that is not perpendicular to the first plane,
   a radiation source mounted to the rotating gantry;
   a first detector array mounted to the rotating gantry; and
   a second detector array mounted to the stationary member.

13. The radiation system of claim 12, wherein:
   a detection surface of the first detector array is substantially arcuate, and
   a detection surface of the second detector array is substantially planar.

14. The radiation system of claim 12, wherein the radiation source overlies the second detector array while the rotating gantry is positioned at a first rotational angle.

15. The radiation system of claim 12, comprising a third detector array mounted to the stationary member.

16. The radiation system of claim 15, wherein:
   the second detector array is mounted to the stationary member under the stationary member, and
   the third detector array is mounted to the stationary member over the stationary member.

17. A method for threat detection, comprising:
   illuminating, via a single radiation source, a first detector array and a second detector array;
   utilizing volumetric data indicative of an object undergoing an examination and yielded from information generated by the first detector array to analyze whether the object is a potential threat object; and
   providing for display a projection image representative of the object to a user, the projection image yielded from information generated by the second detector array.

18. The method of claim 17, wherein the illuminating comprises concurrently illuminating the first detector array and the second detector array.

19. The method of claim 17, comprising:
   varying a relative position of the radiation source and the second detector array during the examination; and
   substantially maintaining a relative position of the radiation source and first detector array during the examination.

20. The method of claim 17, wherein the radiation source is mounted to a rotating gantry configured to rotate about the object during the examination and wherein the illuminating comprises:
   illuminating the second detector array during merely a rotational segment of the rotating gantry.

* * * * *